United States Patent [19]

Hogg

[11] 4,184,766
[45] Jan. 22, 1980

[54] METHOD AND APPARATUS FOR CORRELATING MEASUREMENTS OF TANDEM SENSING ZONES

[75] Inventor: Walter R. Hogg, Miami Lakes, Fla.

[73] Assignee: Coulter Electronics, Inc., Hialeah, Fla.

[21] Appl. No.: 736,546

[22] Filed: Oct. 28, 1976

[51] Int. Cl.² .............................................. G01N 21/00
[52] U.S. Cl. ........................................ 356/72; 356/73
[58] Field of Search .......................... 356/39, 72, 73

[56] References Cited

U.S. PATENT DOCUMENTS

| | | | |
|---|---|---|---|
| 3,822,095 | 7/1974 | Hirschfield | 356/39 |
| 3,924,947 | 12/1975 | Hogg | 356/39 |
| 3,976,862 | 8/1976 | Curbelo | 356/39 |

*Primary Examiner*—Vincent P. McGraw
*Attorney, Agent, or Firm*—Silverman, Cass & Singer, Ltd.

[57] ABSTRACT

A method and apparatus for obtaining information on and identifying particles in a liquid suspension wherein the particles in suspension are moved in a stream through a plurality of sensing zones such that each particle passes through the sensing zones serially. As each particle passes through a sensing zone a particular characteristic of the particle will be measured and its time relationship with the preceding and succeeding particle passing through that zone will also be preserved to form a pattern of time relationships. The pattern of time relationships and the particle characteristics at a particular sensing zone will be correlated with the pattern of time relationships and particle characteristics at either a preceding or succeeding sensing zone in order to correlate all of the characteristics for the particle.

The stream may also be passed to a substrate and the particles laid out on the substrate in a particular spatial pattern. The spatial pattern is also correlated with the time relationships and particle characteristics at the last sensing zone preceding the substrate in order to correlate the particle on the substrate with all of its measured characteristics.

8 Claims, 1 Drawing Figure

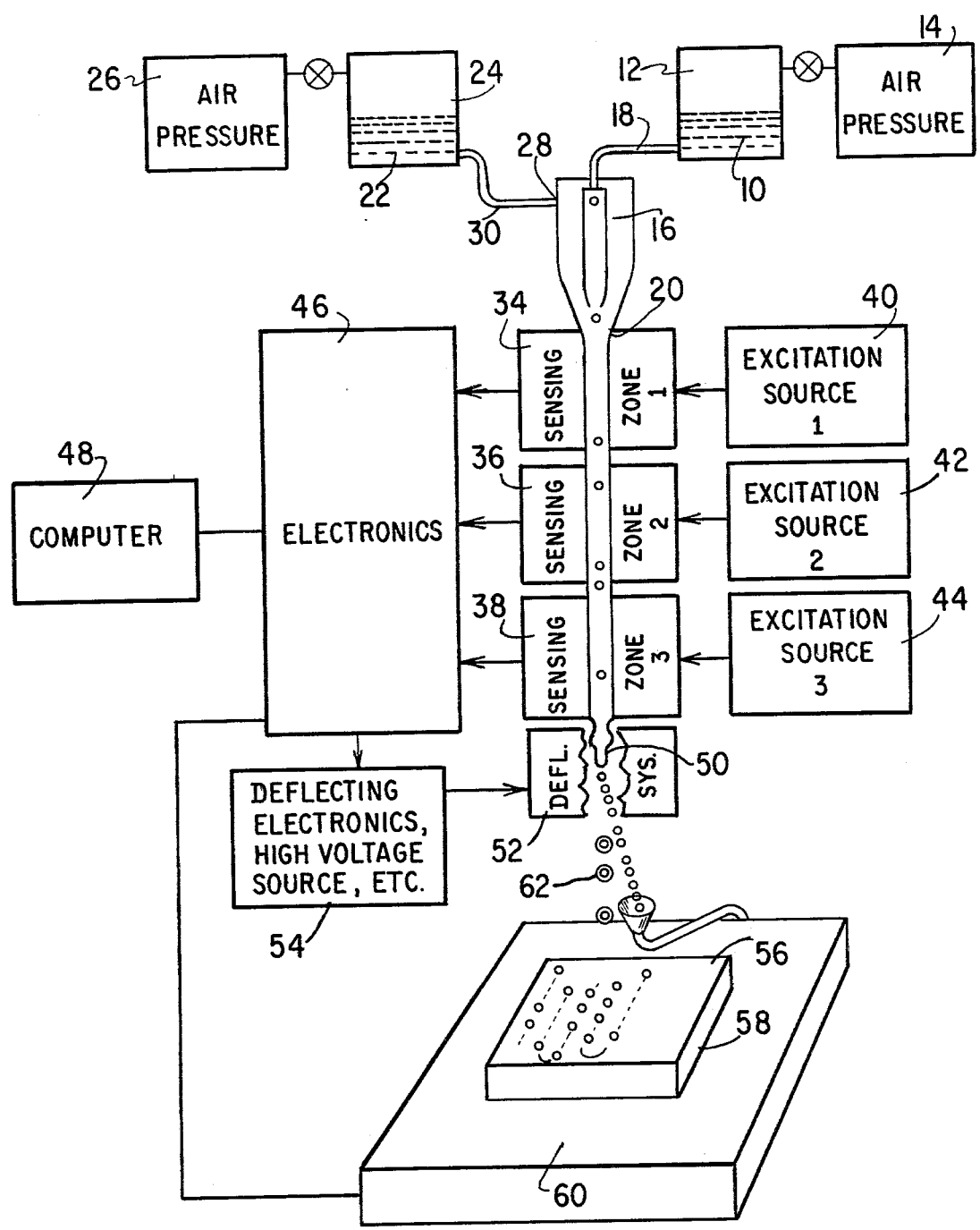

METHOD AND APPARATUS FOR CORRELATING MEASUREMENTS OF TANDEM SENSING ZONES

CROSS-REFERENCE TO RELATED PATENTS

This application is related to U.S. Pat. No. 3,924,947, issued Dec. 9, 1975 to the applicant herein and assigned to the same assignee as this application. This patent is to be considered incorporated by reference into this application to the extent necessary.

BACKGROUND OF THE INVENTION

This invention relates to a method and apparatus for correlating particles and their characteristics, and more particularly to a method and apparatus for correlating a number of separately detected particle characteristics and the particles.

In the fields of particle analysis and particle study it is desirable to ascertain as many characteristics as possible for each particle to be studied. The more characteristics that are determined, the more reliably a machine can distinguish one particle from another somewhat similar particle. This is especially important in areas such as blood analysis where it is desired to distinguish various types of blood cells. The visual classification of blood cells is usually based upon such parameters as color, size and shape of the nucleus after appropriate staining, and the granularity, color and relative quantity of the stained cytoplasm.

Automatic recognition and classification of cells is being pursued today. One method, known as pattern recognition, involves laying out the unknown cells upon a surface or substrate for automatic examination under a high resolution microscope. The microscope viewing field is scanned by some transducer, for example, a vidicon, that responds to the display. The field is scanned and information bits are stored representing the optically detected features of the cells. A computer suitably programmed in accordance with algorithms devised to enable cell identification processes the data from the viewing field in an attempt to match the information with similar information in its memory. This method requires the processing of thousands of bits of information and involves expensive equipment including computers with large storage banks. Notwithstanding the expense and complexity of the equipment involved, absolute accuracy in recognition and classification is not guaranteed, and generally recognition time is quite slow.

A second method, known as a flow-through or simply flow system method, is exemplified by the apparatus in U.S. Pat. No. 2,656,508 which shows a Coulter Counter ®. The mark Coulter Counter is a registered trademark, No. 995,825, of Coulter Electronics, Inc. of Hialeah, Fla. In this method, very rapid measurements are made upon each cell in a liquid suspension as the suspension is flowed through an electrically excited sensing zone. Sensing zones may also be excited by light of one or more colors. The gross parameters which can be measured by this general method are cell volume or size, DNA content, RNA content, color, fluorescence, absorption of light, etc. Sensing zones which measure these gross parameters make what are termed low resolution measurements. Electrically excited sensing zones may utilize not only DC but high frequency AC, as described in U.S. Pat. No. 3,502,974. U.S. Pat. No. 3,497,690 shows a flow through system which combines several measurements in the same sensing zone. Another example of a flow system is given in U.S. Pat. No. 3,960,449 which yields a measurement having to do with size, shape, and internal structure of each cell. These systems are capable of performing a somewhat greater number of measurements and are referred to as intermediate resolution measurements. Flow systems have the great advantage of high speed, measuring in excess of one thousand cells per second, but can only make a limited number of low resolution measurements on each cell.

If it were possible to obtain an increased number of measurements of diverse properties of cells than is presently possible, the probability of correctly identifying specific cells would be greatly enhanced. As each sensing zone is capable of only a low number of measurements several must be used. It is necessary to perform each and every measurement on each cell in order to achieve the ultimate goal of total correlation of all measurements with the cell on which measurements were made. To do this, it is necessary to arrange several sensing zones in series, i.e., in tandem so that the same cell passes through each sensing zone. U.S. Pat. No. 3,822,095 by Hirschfeld is an example of such multiple sensing zones. The problem that arises that the measurements made by the successive sensing zones are not simultaneous. Hence, in order to collate the measurements for classifying the cells, the results of the first-made measurements have to be stored until the last is made.

It is difficult to build other types of sensing zones such that they are less than several centimeters distant from each other. The flow rates used in flow-through systems are commonly on the order of five to ten meters per second and hence it takes from one to two milliseconds for each particle to progress one centimeter down the flow chamber. If mechanical considerations dictate that the sensing zones be spread out over a distance of five centimeters, then the total delay between the first and last sensing zones will be of the order of five to ten milliseconds. To have the particle suspension sufficiently dilute, such that the first sensing zone were precluded from measuring a particle until the last sensing zone had completed its measurement, would require that the minimum spacing between particles would be five centimeters, which corresponds to one-half to one millisecond. The average spacing, considering that the particles are randomly distributed in the suspension, would have to be greatly in excess of five centimeters. Such a weak concentration of particles and very long intervals between particles would vitiate the advantages of the flow system. On the other hand, if the high speed sensing capabilities of flow systems are to be retained, it must be possible to have many particles in such a five centimeter long flow chamber.

Increasing the particle concentration of the sample suspension to utilize fully the high-speed capability of the flow-through method means that the upstream sensing zone will have observed many subsequent particles in the time it takes for a given particle to progress from the first sensing zone to the last. This being the case, the results of measurements of the upstream sensing zones must be stored for later comparison with the measurements at the downstream zone. A problem now presented is how can the machine reliably ascribe the measurements made at the various sensing zones to the proper particle? The obvious solution would be to match the measurement made by the first sensing zone on the very first particle of an aliquot of sample with the very first measurement made at the subsequent and at the last sensing zones, the second with the second, etc., ad infinitum. This would entail storing the first measurement for perhaps a millisecond, but the match would still be made. If the stream of particle-bearing sample were then laid down on an examining surface for subsequent microscopic examination, measurements could be ascribed to the correct particles either by ensuring that the first particle to flow through the flow chamber is the first particle on the examining surface or by the technique disclosed in U.S. Pat. No. 3,924,947.

As is explained in U.S. Pat. No. 3,924,947, depending on each sensing zone to recognize a "first" particle would be risky, and in a device for recognizing types of white cells, or malignant cells, upon which a life-or-death diagnostic decision may be made, no compromise can be tolerated. The risk stems from two sources. First, the sensing zones respond to different properties of the cells. If a first sensing zone responded to fluorescence and a second sensing zone to volume, and the first particle had no fluorescence, the fluorescence of the second particle would be ascribed to the first particle to go through the second sensing zone. The erroneous correlation would then make all following matches erroneous.

Secondly, the practical difficulties of beginning a sample run at the exact instant a first particle entered the first sensing zone, despite hydraulic and electronic starting transients, if not insuperable, would require enormously delicate, fast, and accurate apparatus.

It would seem that the most direct method would be to measure the flow rate of the sample through the flow chamber, and, knowing the distance between the sensing zones, to delay the correlation of measurements by the ratio of that distance to the flow rate. However, the "flow rate" is only the average flow rate. The actual flow in the flow chamber must be laminar to maintain the particle stream. Minor inaccuracies in the centering of the particle stream due to imperfections or dirt on the inner walls of the flow chamber cause minor variations in the delay. Also, the velocity on center is somewhat faster than the average velocity. A fixed delay cannot be relied upon, either.

The flow-through or on-stream method enables some physical separation into groups of cells, exemplified by the apparatus of Fulwyler, U.S. Pat. No. 3,380,584. Thus, cells in each group may be examined independently. Until recently it had not been deemed possible to correlate measurements made on specific cells during an on stream analysis with cells which were measured by pattern recognition methods. U.S. Pat. No. 3,924,947, issued to the inventor of the present application describes an apparatus for correlating the cell characteristics measured on-stream with the cells which are to be measured or have been measured using pattern recognition techniques. The noted patent describes the correlation of information obtained at one sensing zone with the particle locations for the corresponding particles on a substrate.

To summarize, if a number of characteristics are to be ascertained by flow-through technique, different types of sensing zones are employed, each of which detects at least a particular characteristic of the particle. Generally these sensing zones are positioned in series along a flow stream in a manner such as is taught in U.S. Pat. No. 3,822,095.

In such an apparatus, the various sensing zones located along the fluid stream are closely spaced with respect to one another. As each sensing zone is closely spaced to a preceding or succeeding sensing zone, such that their measurements are almost simultaneous, the amount of jitter or randomness in particle arrival time between two adjacent sensing zones is small so that it is simple to correlate particle arrival times and particle characteristics measured at adjacent sensing zones. However, if the various sensing zones are not extremely closely spaced, more sophisticated tactics are called for to ensure that all measurements of a particular particle are in fact ascribed to that particular particle.

If, after passing through the flow chamber bearing several sensing zones, the particles are to be laid out on a substrate for subsequent microscopic examination, a flow chamber-to-substrate correlation must be made. There is no problem in correlating the characteristics measured by the sensing zone closest to the substrate to which the particle is passed with the characteristic ascertained by means of the position of the particle on the substrate. This correlation is taught in the incorporated patent. However, if the sensing zone is not the closest sensing zone to the substrate it is difficult to correlate the characteristic ascertained by that sensing zone with the particle location on the substrate. The difficulty encountered is due to the fact that the flow stream itself is not absolutely stable. That is, there is some jitter or erratic random movement in the flow stream so that the precise timing of the particle movement from each zone to a substrate positioned some distance away is difficult if not impossible to predict. Consequently, correlation with the particle location on the substrate may prove extremely difficult and beyond the capabilities of machines and programs currently available.

The present invention teaches a method for permitting many particles between the first and last sensing zones of such a tandem arrangement of sensing zones without losing track of the identity of each particle and permitting all of the measurements on each particle to be correctly ascribed to that particle. The techniques used, while seeking a different end, are related to the principles upon which the aforementioned U.S. Pat. No. 3,924,947, is based.

SUMMARY OF THE INVENTION

In practicing this invention a method and apparatus is provided for identifying and obtaining information on particles in a liquid suspension. The method requires moving the liquid suspension in a stream through a number of sensing zones which are serially positioned with respect to one another along the flow stream. Each sensing zone operates to measure at least one characteristic of each particle as the particle passes the zone. The sensing zone also measures the temporal relationship of the measured particle with respect to at least one other particle in the flow stream, preferably the preceding or succeeding particle, in order to derive a first sequence of measurements including both relationships of the particles and characteristics of the particles. The temporal relationships portion of the sequence of measurements at each sensing zone is correlated with the temporal relationships portion of the sequence of measurements at an adjacent sensing zone in order to match the particle characteristics for identical particles ascertained at separate sensing zones.

When a particle in suspension has passed through all of the sensing zones the suspension and particle therein will be passed to and laid down upon a substrate such that a pattern of spaced apart particles is formed. The sequence of temporal relationships between individual particles in the stream as they are being laid out determines the sequence of spatial relationships between the individual particles of the laid out pattern. The spatial relationships between individual particles in the laid out pattern are measured to develop a second sequence of measurements which is then correlated with the first sequence of measurements at the last sensing zone to identify a particle in the laid out pattern with its characteristics measured at each sensing zone.

BRIEF DESCRIPTION OF THE DRAWING

The sole FIGURE is an illustration of the invention shown in combined perspective, diagrammatic and block form.

DESCRIPTION OF THE PREFERRED EMBODIMENT

Referring to the FIGURE, a liquid suspension of particles 10 is shown contained in a sample vessel 12 under pressure supplied by an air pressure source 14. The liquid suspension of particles is coupled to a liquid sample entry tube 16 via a conduit 18. The liquid suspension of particles passed through sample entry tube 16 into a flow chamber 20.

A particle free sheath liquid 22 is contained in a sheath liquid vessel 24 which is also maintained under pressure by an air pressure source 26. The sheath liquid 22 in vessel 24 is coupled to a second entry aperture 28 via conduit 30. Sheath fluid entering second entry aperture 28 passes into flow chamber 20 in a laminar or sheath flow surrounding the liquid suspension 10. This causes the liquid suspension and particles therein to flow through flow chamber 20 at the center thereof and at a substantially constant flow rate.

In the preferred embodiment, flow cell 20 has a circular cross section with the largest diameter portion adjacent the tip of sample entry tube 16, tapering to a smaller diameter downstream from that point.

Flow chamber 20 is positioned to pass through three sensing zones 34, 36 and 38. In this embodiment these sensing zones are as described in U.S. Pat. Nos. 3,502,974, 3,946,239 and 3,960,449 for the successive measurement of particle volume and electrical opacity; particle stain uptake and fluorescence; and multiangle light scattering, respectively, although it is to be understood that other types may be employed. Each of these sensing zones requires its own source of excitation energy 40, 42 and 44, respectively, as are described in the noted patents, hereby incorporated by reference. Here the first source is a source of electrical power and the second and third sources are laser beams. Other embodiments will occur to the reader, depending upon the diversity and complexity of the particles to be studied and the required decision-making capability of the apparatus. The electrical signals are coupled to electronics 46 where they are stored and collated for later use for example in sorting cells and the measurements further converted into digital form for permanent storage in computer 48.

In addition to receiving the electrical signal from sensing zone 34, a section of electronics 46 measures the temporal or time relationships of each detected particle with respect to the last preceding particle to be detected. This measured relationship also is converted to digital form and coupled to computer 48 in order to store an entire sequence of temporal relationship measurements for sensing zone 34.

As noted previously, sensing zones 34, 36 and 38 are serially positioned along the length of flow chamber 20, each being spaced as closely as possible to the next sensing zone. However, it will be seen from the noted patents that these spacings must occupy several centimeters. A particle, after it passes along flow chamber 20 through sensing zone 34, passes through a light path of an optical sensing zone 36. The electrical signal produced by sensing zone 36 for that particular particle is coupled to electronics 46 for processing into a form capable of quickly being collated with the signals of the other sensing zones. Once processed into digital form, the information in digital form is coupled to computer 48 for storage.

In addition to receiving and responding to the particle characteristic, electronics 46 measures the temporal or time relationship of this particle with respect to the last preceding particle to be detected by sensing zone 36. The temporal relationship also is converted to digital form and coupled to computer 48 where the entire sequence of measurements related to temporal relationships at sensing zone 36 is stored.

The same particle considered above continues to travel downward through flow chamber 20 passing through a light beam extending between a lens and photocell array 38 and light source 44. Again, the light beam is varied by this passage and the variation is detected producing an electrical signal proportional to the variation. The variation is related to the specific particle characteristic to be measured at this detector and produces an electrical signal that is coupled to electronics 46 in the same manner as sensing zones 34 and 36 for processing into digital form. Additionally, the electrical signal is related to the signal produced by the particle last detected by sensing zone 38 and to the following detected particle by electronics 46 in order to derive a temporal relationship sequence of measurements for sensing zone 38. Both the temporal sequence and particle characteristics are coupled to and stored in computer 48.

In a like manner, the above noted particle passes through and is detected at any additional sensing zones positioned in series along the length of flow cell 20. The particle characteristics detected at these detectors are coupled to and stored in computer 48 along with the temporal relationships between the detected particle and the preceding and succeeding particle detected at that same detector.

In the preferred embodiment illustrated, each particle in suspension, after it has passed through all of the detectors in the flow chamber 20, passes into an ejection nozzle 50 which is vibrated by a vibrational device such as a piezoelectrical transducer 52 operated from power supply 54. Operation of this portion of the apparatus is more fully described in Fulwyler U.S. Pat. No. 3,380,584. The device, however, causes the suspension with particles therein to separate into uniform size droplets which then pass to a substrate 56. The substrate in the embodiment is a microscope slide. Slide 56 is seated on a carriage 58 that is mechanically driven by a driving mechanism 60. The details of this structure are more fully described in the incorporated patent. However, it should be noted that driving mechanism 60 moves carriage 58 in an oscillatory pattern. As a result, the droplets 62 passed to slide 56 form a serpentine pattern on the slide. As the particles in the droplets are laid down upon substrate 56 the temporal intervals combine with the velocity of travel over the serpentine pattern of substrate 56 to create the proportional spatial pattern over the substrate. This spatial pattern is translated back into a temporal pattern, for example, by a scanning microscope as more fully shown and explained in the incorporated pattern, and the temporal patent is coupled to electronics 46 where it is converted into digital form and coupled to computer 48 for storage therein.

The sequence of temporal relationships measured at sensing zone 34 and stored in computer 48 is compared by computer 48 with the sequence of temporal relationships measured by sensing zone 36 and stored in computer 48. The two relationships are easily matched because of the approximately known and constant flow rate and moderate spacing between the sensing zones 34 and 36, that is, the correlation between these two sequences of temporal relationship is relatively simple to accomplish. Once correlated, the characteristics corresponding to the temporal relationships sequence are also correlated and collated by the computer 48.

This same correlation sequence is performed between the sequence of temporal relationships measured by sensing zone 36 and stored in computer 48 and the sequence of temporal relationships measured by sensing zone 38 and stored in computer 48. Again, because of the close spatial relationship between sensing zones 36 and 38, and because they are serially aligned along flow chamber 20 so that each particle passes through these detectors serially, the correlation between the temporal sequence at sensing zone 36 and the temporal sequence at sensing zone 38 is relatively simple to accomplish. The correlation of the temporal sequence measured by the sensing zone 38 with any sensing zone next in series along flow chamber 20 is also performed by computer 48 and all of these correlations may be performed substantially simultaneously after passage through the last sensing zone in order to make a decision to activate a deflection system 52, and on a continuous basis. In the present embodiment, the actuation of the deflection system 52 is made on the presence or absence of particles in the stream at sensing zone 38 so that all particles are saved and only carrier liquid is deflected to waste in order to minimize puddling and motion of captured particles on substrate 56.

As previously noted, the spatial relationships of the particles physically located on substrate 56 also are measured and these measurements are converted back into a temporal sequence which also is stored in computer 48. This sequence of measurements is compared with the temporal sequence of measurements performed at the sensing zone prior to the particles leaving flow chamber 20, so that a correlation between the patterns is possible. When the correlation is achieved, the particle characteristics sensed by the detectors along flow chamber 20 and the physical location of the particles on substrate 56 are correlated. Thus each particle can be located on the substrate and its sensed physical characteristics, stored in the computer, can be correctly ascribed to each particle.

It again must be stressed that correlations between adjacent sensing zones such as, for example, sensing zones 36 and 38, are made rather than correlations between sensing zones 34 and 38 or substrate 56. Correlations between adjacent detectors are preferred in order to minimize variations in time intervals caused by jitter and the distance between corresponding sensing zones. Correlations between other than adjacent sensing zones are much less reliable due to the accumulation of time jitter errors in the temporal sequence at each nonadjacent sensing zone. To minimize the possibility of false correlation and to allow correlation of characteristics determined at a number of separate sensing zones, along with maximum particle concentration to maximize the numbers of particles measured per second, correlation between adjacent sensing zones is greatly to be preferred.

The incorporated patent describes the manner in which a temporal pattern measured at a sensing zone and a temporal pattern measured from a substrate can be correlated. The same type of correlation and the same type of example is applicable to the correlation between adjacent sensing zones and between the last sensing zone along the flow chamber 20 and substrate 56. If a more detailed explanation of such a correlation is desired, reference can be made to the various examples provided in the incorporated patent, including those examples that show an imperfect correlation and how such correlation may be accomplished.

What is desired to be accomplished by Letters Patent of the United States is:

1. A method for obtaining information on the characteristics of particles in a liquid suspension comprising the steps of
    (a) moving the liquid suspension in a stream through a plurality of sensing zones such that each particle passes through the plurality of sensing zones seriatum,
    (b) measuring at each sensing zone at least one characteristic of each particle and the temporal relationship of said each measured particle with at least one other individual particle to derive a sequence of measurements including both those related to temporal relationships and those related to characteristics of individual particles;
    (c) correlating the temporal relationships portion of the sequence of measurements at each sensing zone with one of the temporal relationships portion of the sequence of measurements of at least one of the preceding or succeeding sensing zones to match the particle characteristics at each sensing zone for each particle.

2. The method of claim 1 wherein said plurality of sensing zones includes a first and a last and a number of sensing zones therebetween said step of correlating including correlating the first sensing zone with a second sensing zone and the last with the zone preceding the last, and correlating the temporal portion of the sequence of measurements for each zone between said first and last with one of the preceding and succeeding zones and measurements thereat.

3. The method of claim 1 further including the step of laying said stream of suspension upon a substrate in a pattern of spaced apart particles whereby the sequence of temporal relationships between the individual particles in the stream as they are being laid out determines the sequence of spatial relationships between the individual particles in the laid out pattern, measuring the spatial relationships of the laid out particles between individual particles for a plurality of particles in the laid out pattern to derive a second sequence of measurements and correlating the first sequence of measurements with the second sequence to identify a particle in the laid out pattern with its measured characteristics.

4. The method of claim 1 wherein said correlating is effected on a continuous basis.

5. The method of claim 3 wherein said correlating, measuring and the laying down of said stream on said substrate are effected on a continuous basis.

6. An apparatus for identifying particles in a liquid suspension comprising:

a plurality of sensing means each such sensing means being spaced apart from any other, said particles passing said sensing means seriatim and each said sensing means being operative to measure at least one characteristic of each of said particles as said particles pass through said sensing means, the sequence of said characteristics of said particles at each sensing means having a temporal relationship which forms a first pattern, memory means for storing said first pattern from each sensing means and for storing said measured characteristics, and correlating means for correlating the first pattern from each sensing means and the first pattern from at least one of the preceding or succeeding sensing means so that temporal patterns and particle characteristics are matched with one another.

7. The apparatus of claim 6 further including means for laying said liquid suspension on a substrate in a second pattern whereby the particles in said second pattern have a spatial relationship and said spatial relationship is preserved, said correlating means further operative to correlate the sequence of spatial relationships between particles in said second pattern with the first pattern to match the particles and their characteristics.

8. Apparatus for obtaining information on characteristics of particles in a liquid suspension comprising:

(a) a particle scanning device including
  i. means for containing a quantity of suspension carrying particles,
  ii. a plurality of sensing zones through which pass said particles seriatim said sensing zones each responding to passage of a particle therethrough to produce a signal representing at least one physical characteristic of said particle,
  iii. means for moving the suspension in a stream through the sensing zones such that the particles generate a temporal pattern at each sensing zone, (b) means preserving the temporal pattern and the signals with each signal identified in its temporal pattern with the particular particle producing same on account of the position in the temporal pattern, (c) means for correlating the temporal pattern produced at any sensing zone with a temporal pattern produced at one of the preceding or succeeding sensing zones for matching the particle characteristics sensed at each sensing zone for each particle.

* * * * *